United States Patent [19]

Craft, Sr. et al.

[11] Patent Number: 5,294,305
[45] Date of Patent: Mar. 15, 1994

[54] ETHYLENE GLYCOL RECOVERY PROCESS

[75] Inventors: Frank S. Craft, Sr.; Michael D. Kelly, both of Memphis, Tenn.

[73] Assignee: Mobile Process Technology, Inc., Memphis, Tenn.

[21] Appl. No.: 57,557

[22] Filed: May 6, 1993

[51] Int. Cl.⁵ .................. B01D 3/14; B01D 15/04; C07C 29/74
[52] U.S. Cl. ........................... 203/28; 203/38; 203/41; 203/47; 203/DIG. 25; 568/871; 568/872
[58] Field of Search ............ 203/41, 47, 28, 38, 203/DIG. 25; 568/871, 872, 868

[56] References Cited

U.S. PATENT DOCUMENTS

| | | | |
|---|---|---|---|
| 2,788,373 | 4/1957 | Mills et al. | 260/637 |
| 3,367,847 | 2/1968 | Pierson | 203/41 |
| 3,408,268 | 10/1968 | Pitts et al. | 203/78 |
| 3,491,161 | 1/1970 | Pitts | 260/637 |
| 3,878,055 | 4/1975 | Cox et al. | 203/37 |
| 4,013,519 | 3/1977 | Hoppert et al. | 203/33 |
| 4,046,688 | 9/1977 | Cunningham et al. | 210/37 R |
| 4,118,582 | 10/1978 | Walker | 560/96 |
| 4,605,762 | 8/1986 | Mandoki | 568/868 |

FOREIGN PATENT DOCUMENTS

| | | | |
|---|---|---|---|
| 57-26630 | 2/1982 | Japan | 568/871 |
| 57-26631 | 2/1982 | Japan | 568/871 |

OTHER PUBLICATIONS

EG Purification Plant Test—Old Hickory Plant, Final Report, Oct. 27, 1992.
European patent Application, Publication No. 0463762A2.

Primary Examiner—Wilbur Bascomb, Jr.
Attorney, Agent, or Firm—Ray F. Cox, Jr.

[57] ABSTRACT

The present invention is an improved process for the recovery of ethylene glycol from spent glycol generated in the manufacture of polyethylene terephthalate. The spent glycol typically consists of metal oxide catalyst residues, low molecular weight terephthalate oligomers, diethylene glycol and other trace impurities. The improved process of the present invention is based on the principle that elevating the temperature of the spent glycol increases the solubility of the low molecular weight oligomers so that the low molecular weight oligomers can be dissolved in the ethylene glycol and further that the spent glycol at an elevated temperature may be passed through an ion exchange bed to remove metal oxide catalysts, color forming impurities and other trace impurities.

31 Claims, 1 Drawing Sheet

ETHYLENE GLYCOL RECOVERY PROCESS

BACKGROUND OF THE INVENTION

This invention relates to the removal of impurities found in ethylene glycol recovered from the manufacture of polyethylene terephthalate (PET).

PET is a linear polyester which is generally manufactured in two stages by (1) esterification of terephthalic acid (TPA) with an excess of ethylene glycol (EG) or by the ester exchange reaction of dimethyl terephthalate (DMT) and an excess of EG to form dihydroxyethyl terephthalate (DHET), and (2) the polycondensation of DHET in the presence of a metal oxide catalyst. The metal oxide catalyst is typically an oxide of antimony.

The first stage ester reaction requires an excess of EG. The excess EG is removed during the course of the polycondensation reaction along with other products such as low molecular weight terephthalate oligomers, diethylene glycol (DEG), metal oxide catalysts, typically an oxide of antimony, and trace amounts of other compounds. The EG containing impurities is hereinafter referred to as "spent glycol." The presence of impurities in the spent glycol prevents recycling of the spent glycol into the first stage esterification since product quality would be detrimentally affected thereby. In particular, when product having little or no color is required, spent glycol is unsuitable for recycling.

The prior art on recycling spent glycol relied primarily on flash distillation of the spent glycol as typified by U.S. Pat. Nos. 3,408,268, 3,367,847 and 2,788,373. There are numerous variations to the basic distillation process. For example, U.S. Pat. No. 3,878,085 teaches flash distillation of spent glycol in the presence of an alkali metal hydroxide, while U.S. Pat. No. 3,491,161 teaches the addition of ammonium hydroxide prior to distillation. Some attempts have been made to remove antimony by precipitation prior to distillation of the spent glycol. Typical of these processes are U.S. Pat. Nos. 4,118,582 and 4,013,519.

In practice, spent glycol is purified by distillation in which a pure EG overhead product is recovered. The refined EG is typically sold into the antifreeze market. The still bottoms resulting from the distillation of the spent glycol is a mixture of antimony oxide catalyst, terephthalate oligomers, EG and DEG and various trace impurities such as trace cations, trace anions and color forming impurities.

Significantly, large quantities of still bottoms are generated in the United States each year which presents serious environmental as well as economic problems for PET producers. Furthermore, disposal of the still bottoms as a waste product represents the loss of substantial quantities of EG, DEG, antimony catalysts, and terephthalate oligomers, all of which have commercial value.

There is therefore, a need for a process which removes contaminants from spent glycol and which allows for the recovery and recycle of the still bottoms. Especially desirable is an improved process in which all materials are recycled to either the PET manufacturing process or to other chemical manufacturing processes.

SUMMARY OF THE INVENTION

The present invention is an improved process for the recovery of EG from spent glycol generated in the manufacture of polyethylene terephthalate (PET) wherein terephthalic acid or a lower alkyl ester such as dimethyl terephthalate (DMT) and EG are reacted to form dihydroxyethyl terephthalate (DHET) and said DHET is polymerized in the presence of a metal oxide catalyst such as antimony oxide to form PET and spent glycol containing metal oxide catalyst residues, low molecular weight terephthalate oligomers, diethylene glycol, and other trace impurities, and EG is recovered by fractional distillation and antimony catalyst is recovered, and terephthalate oligomers are recovered for recycle. Ion exchange resins are uniquely suited for the purification of liquids containing ionic contaminants. However, spent glycol is not suitable for being directly introduced into an ion exchange bed due to the presence in the spent glycol at room temperature or thereabouts of solid low molecular weight oligomers. The solids can be removed by filtration, but with a loss in product which is economically unsatisfactory. As noted above some prior art solutions to the problem have relied on the introduction of caustic to cause the solid polymers to dissolve. The improved process of the present invention is based on the principle that elevating the temperature of the spent glycol increases the solubility of the low molecular weight oligomers so that the low molecular weight oligomers can be dissolved in the EG and further that the spent glycol at an elevated temperature may be passed through an ion exchange bed without detrimentally affecting the performance of the ion exchange resin.

The improved process comprises the steps of:

(a) Raising the temperature of the spent glycol to between 50° C. and 160° C. to solubilize the low molecular weight ethylene terephthalate oligomers. The required temperature depends on the amount of low molecular weight oligomers in the spent glycol. Higher temperatures are required to effect the solubilization of higher concentrations of low molecular weight oligomers.

(b) Separating any remaining insolubles from the spent glycol by filtration at a temperature of 50° C. to 160° C.

(c) Passing the spent glycol through activated carbon at a temperature of between 50° C. and 160° C. to remove dissolved color forming impurities.

(d) Passing the spent glycol through a cation exchange resin at a temperature between 50° C. and a maximum temperature tolerable by the resin to remove dissolved antimony compounds as well as other trace cations that may be present.

(e) Passing the spent glycol through a anion exchange resin at between 50° C. and a maximum temperature tolerable by the resin to remove impurities such as phosphates and acetates.

(f) Passing the spent glycol through a mixture of cation/anion exchange resins to remove any trace amounts of impurities.

(g) Optionally, distilling the spent glycol to recover relatively pure EG, DEG and terephthalate oligomers.

The foregoing process can be further improved by recovering the antimony values after the acid regeneration of the cation resin. The antimony salt produced can then be recycled for use in the flame retardant industry and for other commercial end uses.

As an alternative embodiment of the present invention, an equivalent process Can be employed to recover EG, DEG, terephthalate oligomers, and antimony catalysts from still bottoms generated from the present practice of recovering EG by distillation of spent glycol. In this alternative embodiment, the still bottoms are first mixed with EG in an amount sufficient to effect the solubilization of the low molecular weight terephthalate polymers upon elevating the temperature of the spent glycol as set forth in the improved process outlined above.

DETAILED DESCRIPTION OF THE PREFERRED EMBODIMENTS

Figures 1, 2:
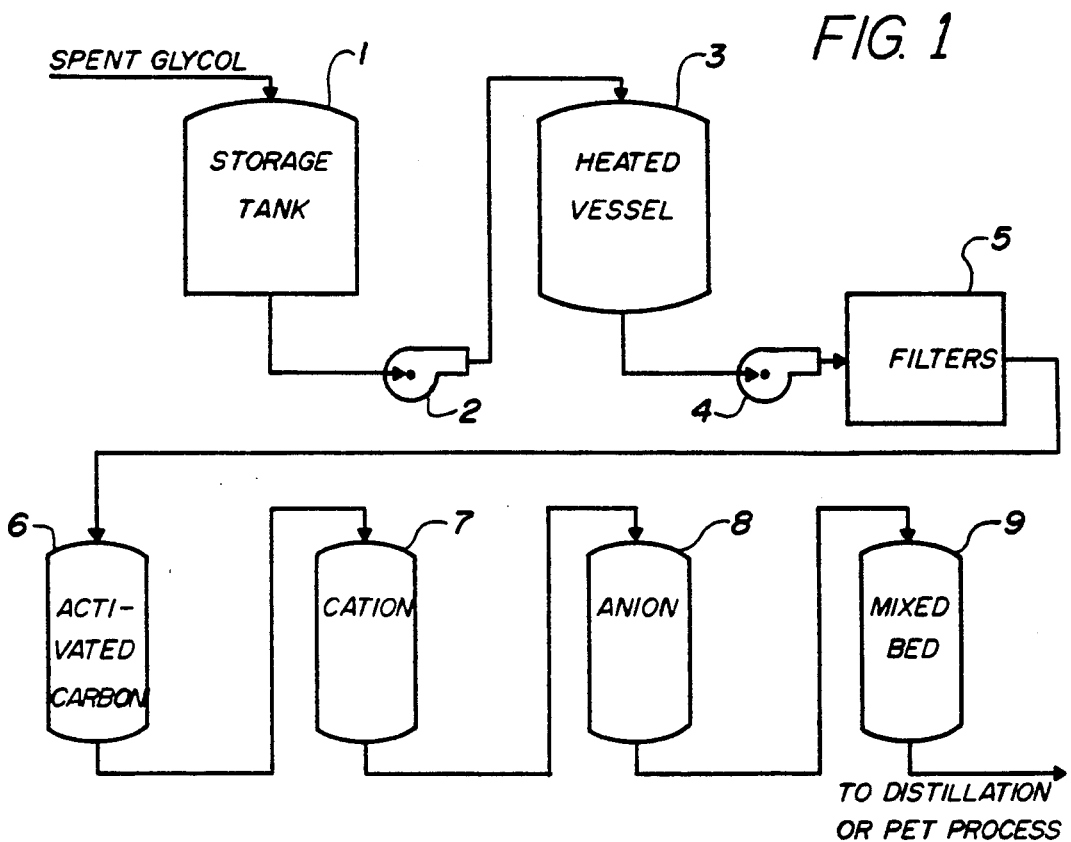
FIG. 1 a block flow diagram of the process of the present invention as it would be practiced for the recovery of spent glycol.
FIG. 2 a block flow diagram of the process of the present invention as it would be practiced for the recovery of still bottoms.

The process of this invention is suitable for the recovery of ethylene glycol, diethylene glycol, antimony and terephthalate polymers from the PET manufacturing process. Spent glycol from the PET process typically contains 90-99% EG, 1-5% DEG, 1-10% low molecular weight terephthalate oligomers, 0.01-0.5% antimony, 2-5% water, a trace of other metallic cations, and a trace of phosphates, acetates and other anions as well as other contaminants.

Low molecular weight terephthalate oligomers are made soluble in the EG by raising the temperature of the spent glycol to a temperature of from about 50° C. to about 160° C. and maintaining this temperature for a sufficient period of time to effect complete or near complete solubilization of the solid material. Some solids may be uneconomical to solubilize and can be removed by filtration. With reference to FIG. 1, spent glycol from the PET process is accumulated in the storage tank 1, from which it is transferred by pump 2 to a steam-heated vessel 3. To effect the glycolysis of higher molecular weight ethylene terephthalate polymers to dihydroxyethyl terephthalate (DHET) and other low molecular weight terephthalyl esters, the glycolysis can be performed in a pressure vessel at an elevated temperature above the boiling point of EG at atmospheric pressure. The temperature and the time required to effect the solubization of the low molecular weight oligomers depends on the amount of low molecular weight oligomers initially present.

The solution of spent glycol and depolymerized PET may contain small amounts of insoluble matter. The insolubles are removed by pumping the solution via pump 4 through the appropriate filter media 5 to remove the particulates. In the process of this invention it is preferred to maintain the fluid temperature from about 50° C. to about 160° C. to effect a lower viscosity solution which results in a lower pressure drop during filtration and to avoid the possibility of precipitation of the terephthalate oligomers. The filter media 5 can be selected from several conventional types, such as bag, cartridge, or tubular filters, provided it is compatible with EG and the pore size is small enough to remove any particulate matter in the spent glycol.

The solution of spent glycol is passed through an activated carbon bed 6 to remove trace quantities of color forming impurities if they are present. In the process of this invention it is preferred to maintain a temperature in the spent glycol of about 50° C. to about 160° C. in the activated carbon bed 6. Although other adsorbents may be used, activated carbon is the preferred adsorbent for the removal of color forming impurities. It is preferrable to use the activated carbon bed 6 ahead of the ion exchange resins 7, 8, 9 so that any dissolved solids leached off the activated carbon will be removed by the ion exchange resins 7, 8, 9.

Soluble metal oxide catalysts, typically antimony compounds, present in the spent glycol are removed by ion exchange with a strong or weak acid cation exchange resin 7. The strong acid cation resin selected can be a ResinTech CG8, Rohm & Haas IR 120, Ionac C-249, a Purolite C100 or similar type. If a weak acid cation resin is selected it can be a ResinTech WACMP, Rohm & Haas IRC-84, Ionac CC, Purolite C-105 or the like. In the process of this invention it is preferred to maintain a temperature in the spent glycol while passing through the cation exchange resin 7 of about 50° to a maximum temperature that the resin can tolerate. Cations resins capable of tolerating up to 85 C. and anion resins capable of tolerating up to 60 C. are known in the art. The present process is, however, not limited to the maximum temperatures tolerable by resins in the present state of the art and it is intended that the scope of the present invention is extended to resins that may hereafter tolerate higher temperatures. Lower temperatures may be desirable however to avoid shortening the lives of the resins to an unacceptable degree. When the cation exchange resin has been exhausted, that is to say, when unacceptable levels of antimony or other cation impurities are present in the effluent stream, the antimony is removed by passing a strong mineral acid such as hydrochloric or sulfuric acid through the cation resin exchange. Typical acid concentrations are 5-25% by weight. The acid regenerate dosage rate can be between 10 to 30 pounds of acid per cubic foot of resin.

Depending on the type of acid regenerant used, various forms of antimony may be recovered. For example, $SbCl_3$ is the form of antimony recovered when HCl is used. Antimony trioxide ($Sb_2O_3$) has wide use principally as a frame retardant for plastics, paints, rubber and textiles. The antimony recovered from the process as antimony trichloride may be converted to antimony trioxide by addition of water to the regenerant solution. In addition to use as a flame retardant, the antimony trioxide is suitable for recycle to an antimony refinery.

Following the removal of the antimony compounds the spent glycol is passed through an anion exchange resin 8 to remove soluble anions such as phosphates and acetates. Some of the antimony catalyst may also be in a form that will be removed by the anion exchange resin. Antimony is considered "amphoteric" in that it acts as either a weak acid or a weak base and thus can exist in either the cation or an anion form. The anion exchange resin 8 can be either a strong base type I or type II. The type I strong base anion resin selected can be a ResinTech SBR, Rohm & Haas IRA-400 or 402, Ionac ASB1 or ASBIP, Purolite A-400 or 600 or the like. The type II strong base anion resin can be a ResinTech SBG2, Rohm Haas IRA-410, Ionac ASB2, Purolite A-300 or the like. Weak base anion resins may be required for the removal of phosphate. In the process of this invention it is preferred to maintain a temperature of the spent glycol through the anion exchange resin 8 of about 50° C. to a maximum temperature tolerable by the the resin. When the anion exchange resin 8 has been exhausted, the resin is regenerated with a strong base such as caustic soda (NaOH). Typical caustic soda concentrations are 6 to 10% with a regenerate dosage rate of 4 to 15 pounds of NaOH per cubic foot of resin.

The spent glycol can be further purified by passing the glycol through a mixed cation/anion resin 9. The resins selected can be from the resins previously described. The use of mixed cation/anion resins 9 is the preferred practice to insure complete removal of soluble impurities. In the process of this invention, it is preferred to maintain a temperature of the spent glycol in the mixed bed resins of about 50° C. to a maximum temperature tolerable by the resins.

The treated EG can, in some cases, be directly recycled into PET manufacturing processes. The presence of minute quantities of impurities that cannot be removed will not in many cases cause detrimental affects on product quality. An example is the presence of small amounts of diethylene glycol (DEG). DEG can be tolerated in some PET polymers without causing product quality problems. Since the process of the present invention removes trace cations and anions as well as color-forming impurities, the treated EG can be directly recycled without requiring distillation to remove the DEG. Distillation to separate DEG from EG is also an option as practiced in the prior art.

An alternative embodiment of the present process may be employed for the recovery of still bottoms. The alternative process is described with reference to FIG. 2. The still bottoms are first mixed with sufficient EG in a reactor 10 to effect the solubization of the solid low molecular weight terephthalate oligomers upon elevating the temperature of the mixture as set forth in the process for the recovery of spent glycol. From this point the process proceeds as set forth in FIG. 1 and described above for the preferred embodiment of the present process.

The present invention is described with reference to various preferred and alternative embodiments, which should be regarded as exemplary and not by way of limitation to the full scope of the present invention as set forth in the appended claims.

What is claimed is:

1. A process for the recovery of ethylene glycol from spent glycol formed in the manufacture of polyethylene terephthalate wherein terephthalic acid or dimethyl terephthalate is reacted with an excess of ethylene glycol to form dihydroxyethyl terephthalate and said dihydroxyethyl terephthalate is polymerized in the presence of a metal oxide catalyst to form polyethlene terephthalate and spent glycol containing metal oxide catalysts, cation impurities and anion impurities, low molecular weight terephthalate oligomers, ethylene glycol and diethylene glycol, comprising the steps of:
    (a) raising the temperature of said spent glycol sufficiently to solubilize said low molecular weight terephthalate oligomers;
    (b) passing said spent glycol at said raised temperature through an ion exchange medium capable of removing said metal oxide catalysts; and
    (c) distilling said spent glycol to recover ethylene glycol, diethylene glycol and terephthalate oligomers.

2. The process of claim 1 wherein the temperature of step (a) is from about 50° C. to about 160° C.

3. The process of claim 1 wherein the distilled ethylene glycol recovered in step (c) is recycled to the manufacturing process.

4. The process of claim 1 wherein said spent glycol contains color forming impurities, said process further comprising, prior to step (b), the step of passing said spent glycol through activated carbon at said raised temperature.

5. The process of claim 1 wherein said spent glycol subsequent to step (a) contains insoluble matter, said process further comprising, immediately following step (a), the step of passing said spent glycol at said raised temperature through a filtration medium capable of removing said insoluble matter.

6. The process of claim 1 wherein said ion exchange medium of step (b) comprises a cation exchange resin to remove said metal oxide catalysts and cation impurities.

7. The process of claim 1 wherein said ion exchange medium of step (b) comprises an anion exchange resin to remove said metal oxide catalysts and anion impurities.

8. The process of claim 1 wherein said ion exchange medium of step (b) comprises both a cation exchange resin and an anion exchange resin.

9. The process of claim 1 wherein said spent glycol contains, subsequent to step (b), trace anion, trace cation and other trace impurities, said process further comprising, subsequent to step (b), the step of passing said spent glycol through a mixed bed ion exchange resin at said raised temperature.

10. The process of claim 4 wherein said spent glycol contains, subsequent to passing through said activated carbon, trace cations, trace anions and other trace impurities, said process further comprising, subsequent to step (b), the step of passing said spent glycol through a mixed bed ion exchange resin at said raised temperature.

11. The process of claim 6 wherein said cation exchange resin is, subsequent to being exhausted, regenerated with acid to recover a salt of said metal oxide catalyst.

12. The process of claim 7 wherein said anion exchange resin is, subsequent to being exhausted, regenerated with an alkaline reagent to recover a salt of said metal oxide catalyst.

13. The process of claim 1 wherein said metal oxide catalysts are oxides of antimony.

14. The process of claim 6 wherein said metal oxide catalysts are oxides of antimony.

15. The process of claim 11 wherein said acid is hydrochloric acid.

16. The process of claim 7 wherein said metal oxide catalysts are oxides of antimony.

17. The process of claim 12 wherein said alkaline reagent is sodium hydroxide.

18. The process of claim 15 wherein said metal oxide catalysts are oxides of antimony.

19. The process of claim 17 wherein said metal oxide catalysts are oxides of antimony.

20. A process for the recovery of ethylene glycol from spent glycol formed in the manufacture of polyethylene terephthalate wherein terephthalic acid or dimethyl terephthalate is reacted with an excess of ethylene glycol to form dihydroxyethyl terephthalate, and said dihydroxyethyl terephthalate is polymerized in the presence of a metal oxide catalyst to polyethylene terephthalate and spent glycol containing metal oxide catalysts, cation and anion impurities, color forming impurities, trace impurities, low molecular weight terephthalate oligomers, ethylene glycol and diethylene glycol, comprising the steps of:
    (a) raising the temperature of said spent glycol to a temperature of from about 50° C. to about 160° C. to solubilize said low molecular weight terephthalate oligomers;

(b) passing said spent glycol through activated carbon at a temperature of from about 50° C. to about 160° C. to remove said color forming impurities;

(c) passing said spent glycol through a cation exchange resin at a temperature of from about 50° C. to a maximum temperature tolerable by said cation exchange resin to remove said metal oxide catalyst and said cation impurities;

(d) passing said spent glycol through an anion exchange resin at a temperature of from about 50° C. to a maximum temperature tolerable by said anion exchange resin to remove said metal oxide catalyst and said anion impurities;

(e) passing said spent glycol through a mixed bed ion exchange resin at a temperature of from about 50° C. to a maximum temperature tolerable by said mixed bed resins; and (f) distilling said spent glycol to recover ethylene glycol, diethylene glycol and terephthalate oligomers.

21. The process of claim 20 wherein the distilled ethylene glycol recovered in step (f) is recycled to the manufacturing process.

22. The process of claim 21 wherein said spent glycol subsequent to step (a), contains insoluble terephthalate oligomers, said process further comprising, immediately following step (a), the step of passing said spent glycol at a temperature of from about 50° C. to about 160° C. through a filtration medium capable of removing said insoluble terephthalate oligomers.

23. The process of claim 21 wherein said metal oxide catalysts are oxides of antimony.

24. The process of claim 23 wherein said cation exchange resin is, subsequent to being exhausted, regenerated with hydrochloric acid to recover antimony trichloride.

25. The process of claim 23 wherein said cation exchange resin is, subsequent to being exhausted, regenerated with sodium hydroxide to recover sodium antimony.

26. A process for the recovery of ethylene glycol, diethylene glycol, metal oxide catalysts and polyethylene terephthalate from still bottoms formed from the distillation of spent glycol formed in the manufacture of polyethylene terephthalate wherein terephthalic acid or dimethyl terephthalate and ethylene glycol are reacted to form dihydroxyethyl terephthalate, said dihydroxyethyl terephthalate is polymerized in the presence of a metal oxide catalyst to form polyethylene terephthalate, and spent glycol containing ethylene glycol, diethylene glycol, low molecular weight terephthalate oligomers and metal oxide catalysts, and ethylene glycol is recovered by distillation from the spent glycol producing still bottoms containing ethylene glycol, diethylene glycol, low molecular weight terephthalate oligomers and metal oxide catalysts, comprising the steps of:

(a) adding ethylene glycol to said still bottoms in an amount sufficient to depolymerize said low molecular weight oligomers upon raising the temperature of said still bottoms;

(b) raising the temperature of said still bottoms sufficiently to depolymerize said low molecular weight terephthalate oligomers;

(c) passing said still bottoms at said raised temperature through an ion exchange medium capable of removing metal oxide catalysts from said still bottoms; and (d) distilling said still bottoms to recover ethylene glycol, diethylene glycol and low molecular weight terephalate oligomers.

27. The process of claim 26 comprising the additional step of regenerating said ion exchange medium of step (c) to recover a salt of said metal oxide catalysts.

28. The process of claim 27 wherein in step (b) said still bottoms are raised to a temperature of from about 50° C. to about 190° C.

29. The process of claim 28 wherein the ion exchange medium of step (c) comprises a combination of cation exchange resins, anion exchange resins and mixed bed resins.

30. The process of claim 29, wherein subsequent to step (b), said still bottoms contain insoluble low molecular weight terephthalate oligomers, comprising the additional step, subsequent to step (b) of passing said still bottoms through a filtration medium capable of removing said insoluble low molecular weight terephthalate oligomers.

31. The process of claim 30, wherein said metal oxide catalysts are oxides of antimony.

* * * * *